US00PP12167P2

(12) United States Plant Patent
Rother

(10) Patent No.: US PP12,167 P2
(45) Date of Patent: Oct. 23, 2001

(54) SCABOSIA PLANT NAMED 'GIANT BLUE'

(76) Inventor: Reinhard W. Rother, P.B. 327, Emerald, Victoria (AU)

( * ) Notice: Subject to any disclaimer, the term of this patent is extended or adjusted under 35 U.S.C. 154(b) by 0 days.

(21) Appl. No.: 09/545,910

(22) Filed: Apr. 9, 2000

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Anne Marie Grunberg
(74) *Attorney, Agent, or Firm*—C. A. Whealy

(57) ABSTRACT

A distinct cultivar of Scabiosa plant named 'Giant Blue', charactrerized by its tall and upright growth habit; freely branching habit; large lavender-colored inflorescences; numerous inflorescences per plant; and long flowering period.

1 Drawing Sheet

BACKGROUND OF THE INVENTION

The present Invention relates to a new and distinct cultivar of Scabiosa plant, botanically known as *Scabiosa anthemifolia*, and referred to by the cultivar name Giant Blue.

The new cultivar is a product of a planned breeding program conducted by the Inventor in Emerald, Victoria, Australia. The objective of the breeding program was to create new Scabiosa cultivars with large and numerous inflorescences.

The new cultivar originated from a cross made by the Inventor of a proprietary selection of *Scabiosa anthemifolia* identified as code number SA 17A as the female, or seed, parent and a proprietary selection of *Scabiosa anthemifolia* identified as code number AU 105, as the male, or pollen, parent. The new Scabiosa was selected by the Inventor as a flowering plant within the progeny of this cross in a controlled environment in Emerald, Victoria, Australia in 1995.

Plants of the new Scabiosa are more vigorous, have shorter peduncles, and have larger inflorescences than plants of the female parent, the selection SA 17A. Plants of the new Scabiosa are larger, have shorter peduncles, and have more inflorescences per plant than plants of the male parent, the selection AU 105.

Asexual propagation of the new cultivar by terminal cuttings at Emerald, Victoria, Australia, has shown that the unique features of this new Scabiosa are stable and reproduced true to type in successive generations.

SUMMARY OF THE INVENTION

The following traits have been repeatedly observed and are determined to be the unique characteristics of 'Giant Blue'. These characteristics in combination distinguish 'Giant Blue' as a new and distinct cultivar:

1. Tall and upright growth habit.
2. Freely branching habit
3. Large lavender-colored inflorescences.
4. Numerous inflorescences per plant.
5. Long flowering period.

The new cultivar can be compared to the *Scabiosa columbaria* cultivar Butterfly Blue, not patented. However in side-by-side comparisons conducted in Emerald, Victoria, Australia, plants of the new cultivar are stronger, have longer peduncles, and have larger inflorescences than plants of the cultivar Butterfly Blue.

The cultivar Giant Blue has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Scabiosa.

The photograph at the top of the sheet comprises a side perspective view of typical flowering plants of 'Giant Blue'.

The photograph at the bottom of the sheet is a close-up view of a typical inflorescence during seed set, a typical mature inflorescence, a typical immature inflorescence, and typical immature and mature leaves of 'Giant Blue'.

DETAILED BOTANICAL DESCRIPTION

The following observations, measurements and values describe 25-cm containers with four plants of the new cultivar grown in Bonsall, Calif., under outdoor, full-sun conditions with day temperatures ranging from 21 to 35° C. and night temperatures ranging from 13 to 18° C.

Color references are made to The Royal Horticultural Society Colour Chart exept where general terms of ordinary dictionary significance are used.

Botanical classification: *Scabiosa anthemifolia* cultivar Giant Blue.

Parentage:

*Female, or seed, parent.*—Proprietary selection of *Scabiosa anthemifolia* identified as code number SA 17A.

*Male, or pollen, parent.*—Proprietary selection of *Scabiosa anthemifolia* identified as code number AU 105.

Propagation:

*Type.*—By terminal cuttings.

*Time to initiate roots.*—About 15 to 25 days at 25° C.

*Rooting habit.*—Fibrous, thick and fleshy.

Plant description:

*Appearance.*—Perennial herbaceous container and garden plant. Upright and tall; inverted triangle; open, airy appearance. Inflorescences held above the foliage on wiry peduncles. Very freely branching with about 10 to 14 lateral branches; removal of terminal apices (pinching) will enhance branching.

*Crop time.*—About 8 to 10 weeks are required to produce a finished, flowering plant in a 10-cm container.

*Vigor.*—Moderate to vigorous.

*Plant height.*—About 60 cm to top of inflorescences.

*Plant spread.*—About 33 cm.

*Lateral branch description.*—Length: About 22 cm. Diameter: About 4 mm. Internode length: About 3.75 cm. Texture: Pubescent; woody at base. Color: 144C.

*Foliage description.*—Leaves opposite; deeply dissected. Quantity of leaves per lateral branch: About 16. Length, fully expanded leaves, basal: About 7.5 cm. Width, fully expanded leaves, basal: About 4.5 cm. Shape: Pinnatifid. Apex: Broadly acute or occasionally tri-lobed. Base: Attenuate, sessile; clasping. Margin: Dentate; irregularly-spaced teeth. Aspect: Somewhat concave. Texture: Pubescence on both surfaces; coarse; somewhat glandular. Color: Young foliage, upper surface: 143A. Young foliage, lower surface: 143B. Fully expanded foliage, upper surface: 144A. Fully expanded foliage, lower surface: 144B. Attenuated leaf base: 143B. Venation, upper surface: 144A. Venation, under surface: 144B.

Inflorescence description:

*Appearance.*—Composite inflorescence form. Solitary inflorescences displayed above and beyond foliage on long wiry peduncles. Disc and ray florets arranged acropetally on a capitulum. Typically three inflorescences per lateral stem. Inflorescences persistent.

*Flowering period.*—Plants flower continuously from March to November in the Northern Hemisphere.

*Inflorescence longevity.*—Inflorescences typically last about one to two weeks on the plant.

*Fragrance.*—None detected.

*Inflorescence size.*—Diameter: About 6 cm. Depth (height): About 2 cm. Diameter of disc: About 4.5 mm.

*Inflorescence buds.*—Length: About 1 cm. Width: About 1.5 cm. Shape: Conical. Color: Just before opening, 145B.

*Ray florets.*—Quantity of ray florets per inflorescence: About 24. Length: About 2.9 cm. Width: About 1.25 cm. Shape: Tubular; zygomorphic; three to five-lobed. Apex: Rounded. Base: Acute. Margin: Entire; ruffled. Texture: Smooth, silky. Color: When opening, upper surface: 76A. When opening, lower surface: 76C to 76D. Fully opened, upper surface: 76A to 76B; fading to 76C. Fully opened, under surface: 76C to 76D.

*Disc florets.*—Quantity of disc florets per inflorescence: About 58. Shape: Tubular; five-lobed. Length: About 1.25 cm. Width: About 5 mm. Color: Immature: 76B. Mature: 76D.

*Phyllaries.*—Quantity per inflorescence and arrangement: About 10 per inflorescence; single star-shaped whorl. Length: About 6 mm. Shape: Narrowly ligulate. Apex: Broadly acute. Margin: Entire. Texture: Somewhat coarse. Color: Upper surface: 138A. Lower surface: 138B to 138C.

*Peduncle.*—Length: About 27 cm. Aspect: Moderately strong; wiry; inflorescences held above and beyond the foliage. Texture: Fine pubescence. Color: 144A to 144B.

*Reproductive organs.*—Androecium: Present on disc florets only. Stamens: Four or five. Anther shape: Elongate ovoid. Anther size: About 3 mm by 0.5 mm. Anther color: 76D. Pollen: Scarce. Pollen color: Lighter than 76D to white. Gynoecium: Present on ray and disc florets. Pistils: One per floret. Pistil length: About 1.4 cm. Stigma shape: Very slightly bi-lobate. Stigma color: 76D. Style length: About 1.1 cm. Style color: Lighter than 76D. Ovary color: 145B.

*Seed.*—Length: About 7 mm. Diameter: About 2 mm. Color: 145B.

Disease resistance: Resistance to pathogens common to Scabiosa has not been observed on plants of the new Scabiosa.

It is claimed:

1. A new and distinct cultivar of Scabiosa plant named 'Giant Blue', as illustrated and described.

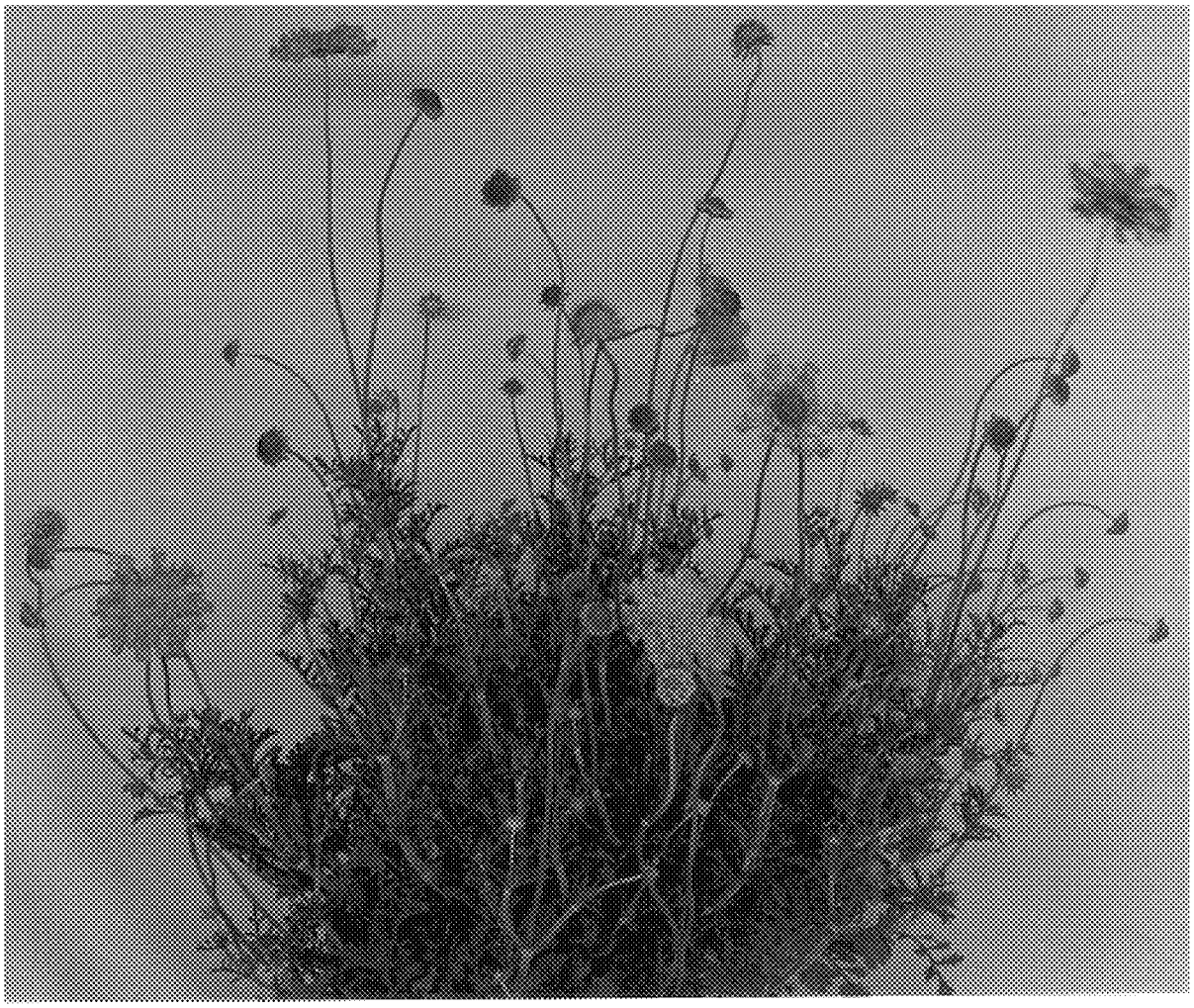
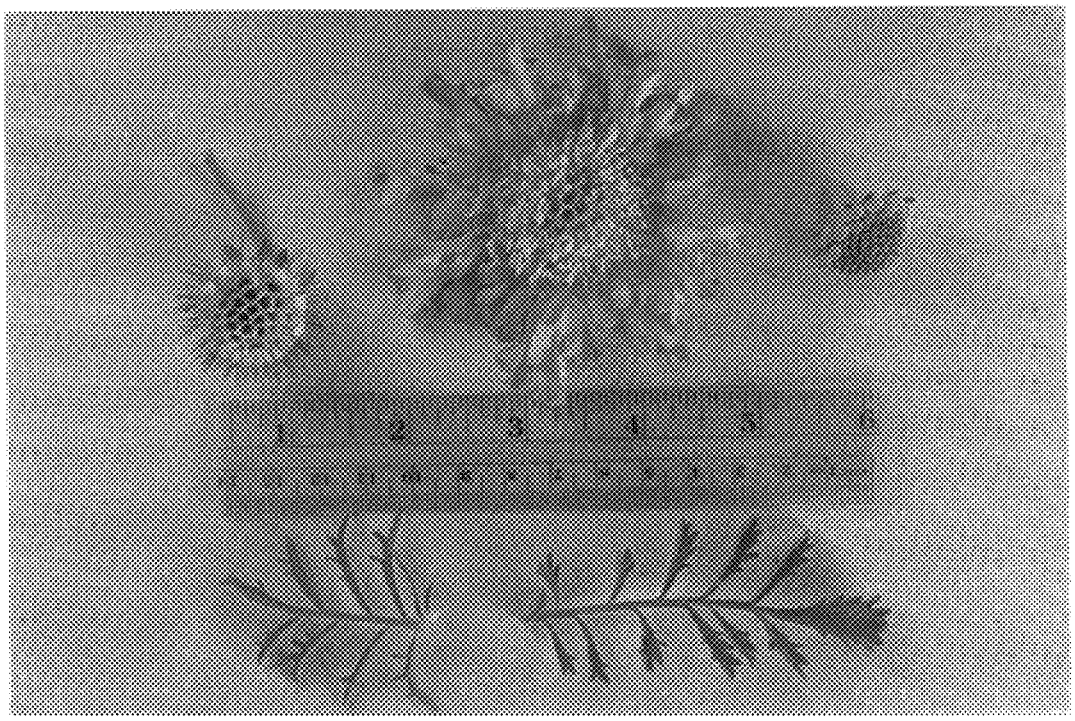

* * * * *